US007226905B2

(12) United States Patent
Viskov

(10) Patent No.: US 7,226,905 B2
(45) Date of Patent: Jun. 5, 2007

(54) PROCESS FOR THE PREPARATION OF CYCLOSPORIN DERIVATIVES

(75) Inventor: Christian Viskov, Ris Orangis (FR)

(73) Assignee: Aventis Pharma S.A., Antony Cedex (FR)

(*) Notice: Subject to any disclaimer, the term of this patent is extended or adjusted under 35 U.S.C. 154(b) by 709 days.

(21) Appl. No.: 09/742,008

(22) Filed: Dec. 22, 2000

(65) Prior Publication Data

US 2001/0025025 A1   Sep. 27, 2001

Related U.S. Application Data

(63) Continuation of application No. PCT/FR99/01480, filed on Jun. 21, 1999.

(30) Foreign Application Priority Data

Jun. 22, 1998 (FR) .................................. 98 07846

(51) Int. Cl.
*A61K 38/13* (2006.01)
*C07K 7/64* (2006.01)

(52) U.S. Cl. ..................... 514/11; 514/9; 530/317; 530/321; 530/335; 530/336; 530/337

(58) Field of Classification Search ............ 514/11, 514/9; 530/317, 321, 335, 336, 337
See application file for complete search history.

(56) References Cited

U.S. PATENT DOCUMENTS 4,703,033 A * 10/1987 Seebach ................. 514/11
4,771,122 A    9/1988 Seebach
4,937,355 A    6/1990 Kloss et al.
5,559,256 A *  9/1996 Gordon et al. ........... 552/303
5,767,069 A    6/1998 Ko et al.
5,994,299 A * 11/1999 Barriere et al. .......... 514/11

FOREIGN PATENT DOCUMENTS

EP   0 194 972   9/1986
EP   0 357 428   3/1990
EP   0 379 063   7/1990
EP   0 484 281   5/1992

OTHER PUBLICATIONS

Seebach et al. , Helvetica Chimica Acta 76, 1564-1590 (1993).*
Seebach et al., "Modification of Cyclosporin A (CS): Generation of an Enolate at the Sarcosine Residue and Reactions with Electrophiles," *Helvetica Chimica Acta*, 76:1564-90 (1993).
T.L. Rathman, "Lithium reagents for syntheses: lithium diisopropylamide and lithium hexamethyldisilazide," *Spec. Chem.*, 9:300-306 (1989).
S.L. Belagali et al., "A highly efficient method of N-methylation for the amino acid derivatives," *Indian J. Chem.*, 34B:45-47 (1995).
K.S. Chu et al., "Asymmetric Total Synthesis of (+)-Jasplakinolide," *J. Org. Chem.*, 56:5196-5202 (1991).

* cited by examiner

*Primary Examiner*—Chih-Min Kam
(74) *Attorney, Agent, or Firm*—Finnegan, Henderson, Farabow, Garrett & Dunner, L.L.P.

(57) ABSTRACT

The invention concerns a novel method for preparing an intermediate polyanion for preparing cyclosporin derivatives by treating a cyclosporin with a hexamethyldisilazane metal salt, optionally in the presence of a metal halide. The treated cyclosporin has one or several free hydroxy groups and/or non-methylated nitrogen atoms in position $\alpha$ and/or any other acid group capable of deprotonation which are optionally deprotonated or in protected form.

12 Claims, No Drawings

PROCESS FOR THE PREPARATION OF CYCLOSPORIN DERIVATIVES

This application is a continuation of International Application No. PCT/FR99/01480, filed Jun. 21, 1999, published as WO 99/67280 on Dec. 29, 1999, which claims priority of French Patent Application 98/07,846, filed Jun. 22, 1998.

The present invention relates to a novel process for the preparation of cyclosporin derivatives modified at the 3-position which comprises treating a cyclosporin with a hexamethyldisilazane metal salt.

Cyclosporins constitute a group of cyclic poly-N-methylated undecapeptides which in most cases possess immunosuppressant, antiinflammatory, and antiparasitic properties but which can also be non-immunosuppressants and can be active with regard to HIV (Human Immunodeficiency Virus).

One of the first natural cyclosporins to have been isolated is known by the name of cyclosporin A, the structure of which is as follows:

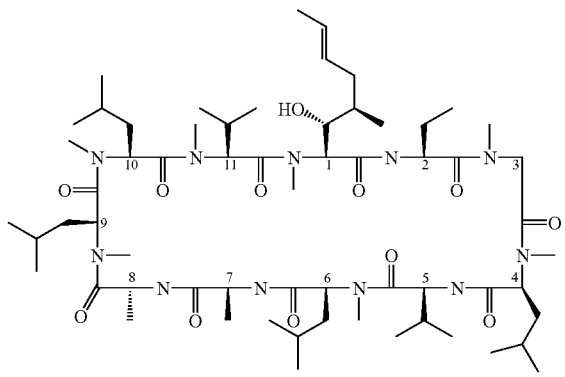

Today, numerous natural cyclosporins are known and isolated (for example, cyclosporins A to Z, hereinafter known as "cyclosporins") and numerous synthetic cyclosporins have been prepared (hereinafter known as "cyclosporin derivatives").

Cyclosporin derivatives modified at the 3-positions can currently be obtained according to the method disclosed in European Patent EP 194,972. This method consists, in particular, in treating, in a first step, a cyclosporin with an organometallic derivative under an inert atmosphere and in then preparing, in a second step, cyclosporin derivatives modified at the 3-position by addition of an electrophilic agent. The main disadvantage of this method lies in the fact that the overall yield is generally extremely low. Furthermore, it is necessary to operate in the presence of a very large excess of electrophile. Furthermore, a significant amount of the S epimer, with respect to the R epimer, is formed by this method and a separation stage is therefore necessary.

Applicant has now shown that the process according to the invention makes it possible to result in cyclosporin derivatives modified at the 3-position with a markedly improved yield. Another advantage of this process lies in the fact that the reaction is carried out at a higher temperature and with a lower excess of electrophile, which facilitates implementation on an industrial scale. Applicant has also demonstrated that the R epimer is formed more selectively.

The present invention thus comprises preparation of a polyanion, which is an intermediate in the preparation of cyclosporin derivatives, by treatment of a cyclosporin with a hexamethyldisilazane metal salt, optionally in the presence of a metal halide.

The polyanion obtained has the general formula:

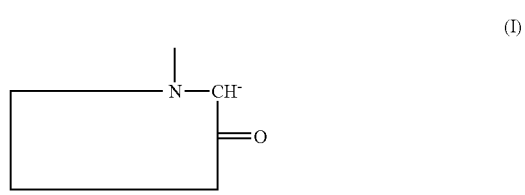

in which

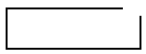

is a cyclosporin in which one or more free hydroxyl groups and/or one or more non-methylated nitrogen atoms at the α position and/or any other deprotonatable acidic group are optionally deprotonated or are in the protected form.

The reaction is generally carried out in an aliphatic or cyclic ether, an aromatic hydrocarbon, or a mixture of these solvents. Mention may be made, by way of example, of tetrahydrofuran (THF), t-butyl methyl ether (TBME), dimethoxyethane (DME), anisole, dioxane, and toluene. The reaction is typically carried out in TBME or in THF in the presence of an aromatic hydrocarbon.

The treatment of the cyclosporin is carried out at a temperature ranging from −40 to 0° C. The reaction is typically initiated at a temperature ranging from −25 to −15° C.

The reaction is carried out according to the invention in the presence of 20 to 30 molar equivalents of hexamethyldisilazane metal salt, and usually between 23 and 28 molar equivalents. The hexamethyldisilazane metal salt can be, by way of example, a hexamethyldisilazane alkali metal salt. Typically, it can be the hexamethyldisilazane lithium salt, the hexamethyldisilazane sodium salt, or the hexamethyldisilazane potassium salt. The reaction is usually carried out in the presence of the hexamethyldisilazane lithium salt.

According to an alternative form of the invention, the preparation of the cyclosporin polyanion can be carried out in the presence of at least one metal halide. The at least one metal halide can, for example, be lithium chloride, caesium chloride, caesium fluoride, mercuric chloride, cuprous chloride, and the like. The reaction can be carried out in the presence of from 2 to 8 molar equivalents of caesium or lithium chloride, and can be carried out in the presence of from 5 to 7 molar equivalents of caesium chloride.

Furthermore, the ratio (weight/weight) of cyclosporin involved with respect to the total weight of the solution is generally less than or equal to 10%. The reaction is typically carried out with a cyclosporin ratio of less than or equal to 6%. Usually, between 2 and 5% of cyclosporin is introduced.

According to another aspect of the present invention, the polyanion obtained has the formula:

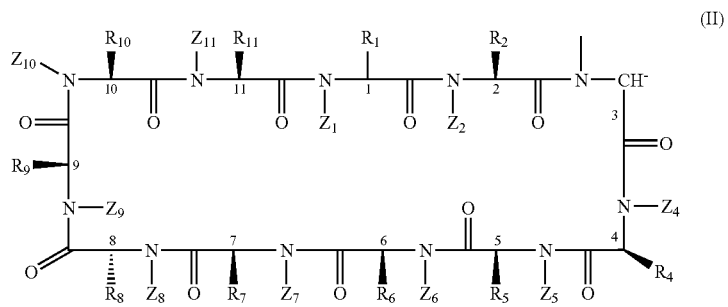

(II)

in which:
i) the radicals $R_1$, $R_2$, and $R_4$ to $R_{11}$, and $Z_1$, $Z_2$, and $Z_4$ to $Z_{11}$ are defined as for cyclosporin A; or
ii) the radicals $R_1$, $R_2$, and $R_4$ to $R_{11}$, and $Z_1$, $Z_2$, and $Z_4$ to $Z_{11}$ are defined as for cyclosporin A, with the exception of $R_4$ and $Z_4$, which are defined so as to have, at the 4-position, the amino acid 4'-hydroxy-methylleucine; or
iii) the radicals $R_2$ and $R_5$ to $R_{11}$, and $Z_2$ and $Z_5$ to $Z_{11}$ are defined as for cyclosporin A; and
$Z_1$ is a methyl group and $R_1$ has the formula:

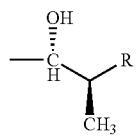

(IIIa)

in which R is a radical of formula —$CH_2$—CH=CH—$CH_2$—R' in which R' is an alkylthio, aminoalkylthio, alkylaminoalkylthio, dialkylaminoalkylthio, pyrimidinylthio, thiazolylthio, N-alkylimidazolylthio, hydroxyalkylphenylthio, hydroxyalkylphenyloxy, nitrophenylamino, or 2-oxopyrimidin-1-yl radical; or
R is a radical of formula —$CH_2$—S-Alk in which Alk is an alkyl group; and
$Z_4$ and $R_4$ are radicals such that there is, at the 4-position, an amino acid methyl leucine (MeLeu) or 4'-hydroxy-MeLeu; or
iv) $Z_1$ and $R_1$ are radicals such that there is, at the 1-position, a substituted homothreonine of general formula:

$R_i$—$CH_2CH(CH_3)$—CH(OH)—CH(NHCH$_3$)—COOH    (IIIb)

in which $R_i$ is n-propyl or propenyl and the double bond usually exhibits a trans configuration; and
$R_2$ and $Z_2$ are radicals such that there is, at the 2-position, α-aminobutyric acid (αAbu), valine (Val), norvaline (Nva), or threonine (Thr); and
$R_4$ and $Z_4$ are radicals such that there is, at the 4-position, N-methyl-γ-hydroxyleucine or N-methyl-γ-acetyloxy-leucine; and
$R_5$ and $Z_5$ are radicals such that there is, at the 5-position, Val; and
$R_6$, $Z_6$, $R_9$, $Z_9$, $R_{10}$, and $Z_{10}$ are radicals such that there is, at the 6-, 9-, and 10-positions, N-MeLeu; and
$Z_7$ and $R_7$ are radicals such that there is, at the 7-position, alanine (Ala); and $Z_8$ and $R_8$ are radicals such that there is, at the 8-position, D-Ala or D-serine; and
$Z_{11}$ and $R_{11}$ are radicals such that there is, at the 11-position, N-methylvaline; or
v) $Z_1$ and $R_1$ are radicals such that there is, at the 1-position, a methyl (4R)-4-[(E)-2-butenyl]-4-methyl-L-threonine (MeBmt) radical or a radical having the general formula:

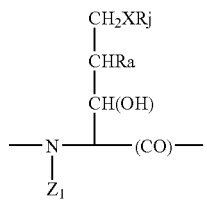

(IIIc)

in which $R_j$ is a hydrogen atom or a lower alkyl radicals, a lower alkenyl, a lower haloalkyl, an aryl, a lower alkyloxy, an alkoxy$C_{1-6}$alkyl, a hydroxymethyl, a lower alkylthio, an alkylthio$C_{1-6}$alkyl, a $C_{1-6}$ mercaptoalkyl, or a heteroaryl;
it being possible for the aryl and heteroaryl radicals to be substituted with one or more functional groups chosen from: $C_{1-6}$ alkyl; $C_{1-6}$ alkanoyl; $C_{1-6}$ haloalkyl; halo; cyano; $C_{1-3}$ hydroxyalkyl; $C_{1-6}$ alkyloxy; $C_{1-6}$ alkyl-S(O)$_n$, where n=0, 1, or 2; NR$_b$-COR$_c$, in which R$_b$ and R$_c$ independently are H or a $C_{1-6}$ alkyl, —NO$_2$, —NR$_b$R$_c$, —OR$_b$, —CONR$_b$R$_c$, —COR$_b$, —NR$_b$CONR$_b$R$_c$, NR$_b$COR$_c$, —OCOR$_b$, —SCOR$_b$, or —OCH$_2$O—; and
$R_a$ is a lower alkyl; and
$Z_1$ is a lower alkyl, a lower phenylalkyl, or an aryl; and
X is S, SO, SO$_2$, O, or NR$_b$; and
$Z_2$ and $R_2$ are radicals such that there is, at the 2-position, the amino acid L-2-aminobutyric acid, Nva, L-Thr, or the same amino acid as at the 1-position; and
$Z_4$ and $R_4$ are radicals such that there is, at the 4-position, the amino acid N-methyl-L-leucine; and
$Z_5$ and $R_5$ are radicals such that there is, at the 5-position, the amino acid L-Val or Nva; and
$Z_6$ and $R_6$ are radicals such that there is, at the 6-position, the amino acid N-methyl-L-leucine; and
$Z_7$ and $R_7$ are radicals such that there is, at the 7-position, the amino acid L-Ala, L-2-aminobutyric acid, or L-phenylalanine; and
$Z_8$ and $R_8$ are radicals such that there is, at the 8-position, the amino acid D-Ala or L-Ala; and $Z_9$ and $R_9$ are radicals such that there is, at the 9-position, the amino acid N-methyl-L-leucine or N-methyl-L-Val; and $Z_{10}$ and $R_{10}$ are radicals such that there is, at the 10-position, the amino acid N-methyl-L-leucine or L-leucine; and $Z_{11}$ and $R_{11}$ are radicals such that there is, at the 11-position, the amino acid N-methyl-L-Val, L-Val, or L-2-aminobutyric acid; or vi) the radicals $R_4$ to $R_{11}$ and $Z_4$ to $Z_{11}$ are defined as for cyclosporin A; and $Z_1$ and $R_1$ are radicals such that there is, at the 1-position, the amino acid MeBmt or dihydro-MeBmt; and $Z_2$ and $R_2$ are radicals such that there is, at the 2-position, the amino acid αAbu, Thr, Val, or Nva; or vii) the radicals $R_7$ to $R_{11}$ and $Z_7$ to $Z_{11}$ are defined as for cyclosporin A; and $Z_1$ and $R_1$ are radicals such that there is, at the 1-position, the amino acid MeBmt, dihydro-MeBmt, or 8'-hydroxy-MeBmt; and $Z_2$ and $R_2$ are radicals such that there is, at the 2-position, the amino acid αAbu, Val, Thr, Nva, or MeOThr; and $Z_4$ and $R_4$ are radicals such that there is, at the 4-position, the amino acid MeLeu, γ-hydroxy-MeLeu, MeIle, MeVal, MeThr, MeAla, MeaIle, or MeaThr; and $Z_5$ and $R_5$ are radicals such that there is, at the 5-position, the amino acid Val, Leu, MeVal, or MeLeu; and $Z_6$ and $R_6$ are radicals such that there is, at the 6-position, the amino acid MeLeu, γ-hydroxy-MeLeu, or MeAla;

provided that, when $R_4$ and $Z_4$ are MeLeu, then $R_5$ and $Z_5$ are MeVal or MeLeu, or $R_1$ and $Z_1$ are 8'-hydroxy-MeBmt; or viii) the radicals $R_1$, $R_2$, and $R_4$ to $R_{11}$, and $Z_1$, $Z_2$, and $Z_4$ to $Z_{11}$ define a cyclosporin in which the 3' carbon of the residue at the 1-position or the β carbon of the residue at the 2-position is substituted by O-acyl or oxo; and $Z_1$ and $R_1$ are radicals such that there is, at the 1-position, a residue of general formula

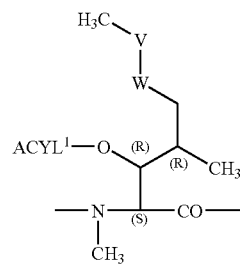

(IIId)

in which —V—W— is $CH_2$—$CH_2$ or trans CH=CH, and $ACYL^1$ is an acyl group; and $Z_2$ and $R_2$ are radicals such that there is, at the 2-position, an amino acid αAbu, Val, Thr, Nva, or a β-O-acylated α-amino acid and $Z_5$ and $R_5$ are radicals such that there is, at the 5-position, an amino acid Val or Nva when there is simultaneously an amino acid Nva at the 2-position; and $Z_8$ and $R_8$ are radicals such that there is, at the 8-position, an amino acid D-Ala or a β-O-acylated or β-hydroxylated α-amino acid having the D configuration; and the radicals at the 4-, 6-, 7-, and 9- to 11-positions are defined as for cyclosporin A; and one or more hydroxyl groups and/or one or more non-methylated nitrogen atoms at the α position and/or any other deprotonatable acidic group present in general formula (II) are optionally deprotonated or are optionally in the protected form.

The polyanions of general formula (II) resulting from the process according to the invention are useful as intermediates in the preparation of cyclosporin derivatives of general formula:

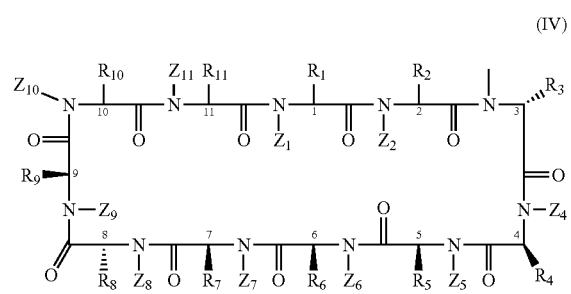

(IV)

in which:
1) the radicals $R_1$ to $R_{11}$ and $Z_1$ to $Z_{11}$ are as defined above in i) and $R_3$ is a radical —S-Alk-R° in which:

Alk is an alkylene radical comprising from 2 to 6 straight- or branched-chain carbon atoms or a cycloalkylene radical comprising from 3 to 6 carbon atoms; and R° is
a carboxyl or alkyloxycarbonyl radical; or
an —$NG_1G_2$ radical in which $G_1$ and $G_2$, which are identical or different, are each
a hydrogen atom; or
a phenyl, cycloalkyl ($C_{3-6}$), alkenyl ($C_{2-4}$), or alkyl radicals, each of which is optionally substituted by a halogen atom, or an alkyloxy, alkyloxycarbonyl, amino, alkylamino, or dialkylamino radical; or
a benzyl radical or a saturated or unsaturated heterocyclyl radical comprising 5 or 6 ring members and from 1 to 3 heteroatoms; or
$G_1$ and $G_2$ form, with the nitrogen atom to which they are attached, a saturated or unsaturated heterocycle comprising from 4 to 6 ring members which can comprise another heteroatom chosen from nitrogen, oxygen, and sulphur and which is optionally substituted by alkyl, phenyl, or benzyl; or
a radical of general formula:

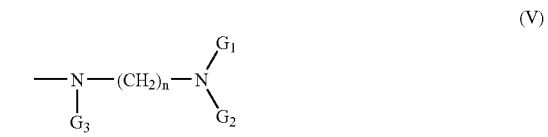

(V)

in which $G_1$ and $G_2$ are defined as above, $G_3$ is a hydrogen atom or an alkyl radical, and n is an integer from 2 to 4, and the alkyl portions or radicals defined above are straight or branched and comprise from 1 to 4 carbon atoms; or 2) the radicals $R_1$ to $R_{11}$ and $Z_1$ to $Z_{11}$ are as defined above in ii) and $R_3$ is —S—$CH_3$ or a radical —S-Alk-R° in which:

Alk is an alkylene radical comprising from 2 to 6 straight- or branched-chain carbon atoms or a cycloalkylene radical comprising from 3 to 6 carbon atoms; and R° is a hydroxyl, carboxyl, or alkyloxycarbonyl radical; or
an —NG$_1$G$_2$ radical or a radical of general formula:

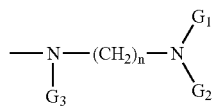

(V)

as defined above;

3) the R$_1$ to R$_{11}$ and Z$_1$ to Z$_{11}$ radicals are as defined above in iii) and R$_3$ is a radical of structure —S-Alk-R° in which:

Alk is an alkylene radical comprising from 2 to 6 straight- or branched-chain carbon atoms or a cycloalkylene radical comprising from 3 to 6 carbon atoms; and R° is a hydrogen atom or a hydroxyl, carboxyl, or alkyloxycarbonyl radical; or an —NG$_1$G$_2$ radical in which G$_1$ and G$_2$, which are identical or different, are each a hydrogen atom; or a phenyl, cycloalkyl (C$_{3-6}$), or alkyl radical, each of which is optionally substituted by a halogen atom, or an alkyloxy, alkyloxycarbonyl, amino, alkylamino, or dialkylamino radical; or a benzyl radical or a saturated or unsaturated heterocyclyl radical comprising 5 or 6 ring members and from 1 to 3 heteroatoms; or G$_1$ and G$_2$ form, with the nitrogen atom to which they are attached, a 5- or 6-membered heterocycle which can comprise another heteroatom chosen from nitrogen, oxygen, and sulphur, and which is optionally substituted by alkyl; or a radical of general formula:

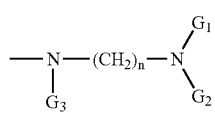

(V)

as defined above; or 4) the radicals R$_1$ to R$_{11}$ and Z$_1$ to Z$_{11}$ are as defined above in iv) and R$_3$ is a radical chosen from:

straight or branched alkyl (C$_{2-6}$), alkenyl, or alkynyl radicals, each of which is optionally substituted by a hydroxyl, amino, C$_{1-4}$ alkylamino, C$_{1-3}$ dialkylamino, alkyloxy, or acyloxy group;

COOG$_4$ or CONHG$_4$, in which G$_4$ is a straight or branched alkyl comprising from 1 to 4 carbon atoms;

—Y—G$_5$, in which Y is S or O and G$_5$ is a straight or branched C$_{1-4}$ alkyl, a straight or branched alkenyl, or a straight or branched alkynyl, and in which, if Y is S, G$_5$ can also be an aryl or a heteroaryl;

a halo or cyano group; and

CHG$_6$G$_7$, in which G$_6$ is a hydrogen atom or a methyl, ethyl, or phenyl group, and G$_7$ is a hydrogen atom or a hydroxyl, halo, amino, C$_{1-4}$ alkylamino, C$_{1-4}$ dialkylamino, acyloxy, t-butoxycarbonylaminoethoxyacetyloxy, or alkyloxycarbonyl group; or 5) the radicals R$_1$ to R$_{11}$ and Z$_1$ to Z$_{11}$ are as defined above in v) and R$_3$ is a radical such that there is, at the 3-position, an α-(methylmercapto)sarcosyl or N-methyl-D-alanyl residue; or 6) the radicals R$_1$ to R$_{11}$ and Z$_1$ to Z$_{11}$ are as defined above in vi) and R$_3$ is a C$_{1-6}$alkyl, haloC$_{1-6}$alkyl, hydroxyC$_{1-6}$alkyl, mercaptoC$_{1-6}$alkyl, aminoC$_{1-6}$alkyl, C$_{2-5}$alkoxycarbonylamino(C$_{1-4}$alkyl), nitroC$_{1-6}$alkyl, cyanoC$_{1-5}$alkyl, C$_{1-6}$alkoxy(C$_{1-6}$alkyl), C$_{1-6}$alkylthio-(C$_{1-6}$alkyl), C$_{2-7}$alkanoyloxy(C$_{1-6}$alkyl), C$_{2-7}$diazoalkanoyloxy(C$_{1-6}$alkyl), carboxy(C$_{1-6}$alkyl), C$_{2-7}$alkoxycarbonyl(C$_{1-6}$alkyl), aminocarbonyl(C$_{1-4}$alkyl), aminocarbonyloxy(C$_{1-4}$alkyl), amino(C$_{1-4}$alkanoyloxy)(C$_{1-4}$alkyl), amino(C$_{2-9}$alkoxycarbonyl)(C$_{1-4}$alkyl), C$_{2-7}$alkylcarbonyl, C$_{2-7}$alkoxycarbonyl, C$_{1-6}$alkylthio, hydroxyC$_{1-6}$alkylthio, C$_{1-6}$alkoxy(C$_{1-6}$alkylthio), C$_{2-11}$alkanoyloxy(C$_{2-4}$alkylthio), C$_{2-11}$alkanoyloxy(C$_{2-4}$alkylsulphinyl), C$_{2-11}$alkanoyloxy(C$_{2-4}$alkylsulphonyl), aminocarbonyloxy(C$_{2-4}$alkylthio), C$_{2-11}$aminoalkanoyloxy(C$_{2-4}$alkylthio), aminocarbonyloxy(C$_{2-4}$alkylsulphinyl), aminocarbonyloxy(C$_{2-4}$alkylsulphonyl), aminoalkanoyloxy(C$_{2-4}$alkylsulphinyl), aminoalkanoyloxy(C$_{2-4}$alkylsulphonyl), aminocarbonyl, C$_{3-6}$alkenyl, C$_{3-6}$alkynyl, haloC$_{3-6}$alkenyl, haloC$_{3-6}$alkynyl, hydroxyC$_{3-6}$alkenyl, aryl(C$_{1-6}$alkyl), hydroxylated aryl(C$_{1-6}$alkyl), aryl(C$_{3-6}$alkenyl), aryl(C$_{3-6}$alkynyl), hydroxylated aryl(C$_{3-6}$alkenyl), hydroxylated aryl(C$_{3-6}$alkynyl), arylthio, heteroarylthio, aryl(C$_{2-5}$alkoxycarbonylamino)(C$_{1-4}$alkyl), halo, or cyano radical, or a radical of formula Q—(CH$_2$—CH$_2$—O)$_n$—CO—O—CH$_2$—, in which n is 1, 2, or 3 and Q is amino; or 7) the radicals R$_1$ to R$_{11}$ and Z$_1$ to Z$_{11}$ are as defined above in vii) and R$_3$ is a radical such that there is, at the 3-position, an amino acid D-MeAla; or 8) the radicals R$_1$ to R$_{11}$ and Z$_1$ to Z$_{11}$ are as defined above in viii) and R$_3$ is a radical such that there is, at the 3-position, an α-amino acid which is N-methylated at the α position and which has the D configuration.

The cyclosporin derivatives of general formula (IV) can be obtained by addition of an electrophilic agent to a polyanion of general formula (II). When the radicals of this agent can interfere with the reaction, it is typical to protect them beforehand with compatible radicals which can be put in place and removed without affecting the remainder of the molecule. The addition can be followed, if appropriate, by stages of separation and purification of the cyclosporin derivative of formula (IV) according to methods known to a person skilled in the art.

The cyclosporin derivatives of general formula (IV), the radicals of which are defined as in 1), 2), 3), or 4), in which R$_3$ is S—G$_5$, can be obtained by addition to a polyanion of general formula (II) of a disulphide of general formula

G—S—S—G (VI)

in which G is Alk-R° or G$_5$ as defined above in 1), 2), 3), or 4). The functional groups of the polyanion which can interfere with the reaction can, if appropriate, be protected beforehand, followed by removal, if appropriate, of the protective radical/radicals.

The disulphide of general formula (VI) is generally added either pure or in solution in an organic solvent, such as an aliphatic or cyclic ether (for example, THF, TBME, or DME) or a hydrocarbon (for example, toluene), at a temperature ranging from −40 to 0° C.

The addition of the disulphide is typically carried out at a temperature ranging from −25 to −15° C., inclusive.

After addition of the disulphide of general formula (VI), the reaction mixture can be brought to a temperature of greater than 0° C. The reaction mixture is usually maintained at a temperature ranging from 0 to 30° C. and the progress of the reaction is monitored according to methods known to a person skilled in the art. More typically, the reaction mixture is maintained at a temperature ranging from 15 to 25° C., inclusive.

The disulphide of general formula (VI) can be obtained from two equivalents of a compound of general formula G—SH in which G is Alk-R° or $G_5$ as defined above in 1), 2), 3), or 4). The reaction can be carried out in an oxidizing medium, in an organic solvent (for example, in diethyl ether or in dichloromethane), or in an alcohol (for example, methanol or ethanol), and in the presence of an alkali metal hydroxide. The oxidizing medium is typically obtained by passing oxygen or by addition of diiodine in an organic solvent, for example, diethyl ether. The alkali metal hydroxide is typically sodium hydroxide.

When the radicals of the G radical can interfere with the reaction, it is preferable to protect them beforehand with compatible radicals which can be put in place and removed without affecting the remainder of the molecule. Furthermore, the hydroxyl radicals present on the cyclosporin can optionally be protected with any group which does not interfere with the reaction.

By way of example, the protective groups can be chosen from the radicals described by T. W. Greene, *Protective Groups in Organic Synthesis*, J. Wiley-Interscience Publication (1991), or by McOmie, *Protective Groups in Organic Chemistry*, Plenum Press (1973), the disclosure of each of which is specifically incorporated by reference herein.

In the general formula (V), when $G_1$ and/or $G_2$ are a heterocyclyl group, the latter can be chosen from pyridyl, tetrahydropyridyl, piperidyl, imidazolyl, oxazolyl, and thiazolyl.

When $G_1$ and $G_2$ form a heterocycle with the nitrogen atom to which they are attached, the heterocyclyl radical can be chosen, by way of example, from azetidinyl, piperidyl, piperazinyl, N-methylpiperazinyl, N-phenylpiperazinyl, N-benzylpiperazinyl, pyridyl, imidazolyl, morpholino, thiomorpholino, tetrahydropyridyl, methyltetrahydropyridyl (for example, 4-methyltetrahydropyridyl), and phenyltetrahydro-pyridyl (for example, 4-phenyltetrahydropyridyl).

The thioalkylation reaction can be followed, if appropriate, by stages of separation and/or purification of the cyclosporin derivative of general formula (IV) according to methods known to a person skilled in the art. Typically, they can be carried out by methods such as crystallization or chromatography.

The derivatives of general formula (IV), in which the radicals $R_1$ to $R_{11}$ and $Z_1$ to $Z_{11}$ are as defined in 4), with the exception of $R_3$ which is S—$G_5$, can be obtained from the polyanion according to the invention by the methods disclosed in Patent Application WO 97/04005, the disclosure of which is specifically incorporated by reference herein, or by any other equivalent method.

The derivatives of general formula (IV), in which the radicals $R_1$ to $R_{11}$ and $Z_1$ to $Z_{11}$ are as defined in 5), can be obtained from the polyanion according to the invention by analogy with the methods disclosed in Patent Application EP 194,972, the disclosure of which is specifically incorporated by reference herein.

The derivatives of general formula (IV), in which the radicals $R_1$ to $R_{11}$ and $Z_1$ to $Z_{11}$ are as defined in 6), can be obtained from the polyanion according to the invention by the methods disclosed in Patent Application EP 194,972, or by any other equivalent method.

The derivatives of general formula (IV), in which the radicals $R_1$ to $R_{11}$ and $Z_1$ to $Z_{11}$ are as defined in 7), can be obtained from the polyanion according to the invention by analogy with the methods disclosed in Patent Application EP 194,972.

The derivatives of general formula (IV), in which the radicals $R_1$ to $R_{11}$ and $Z_1$ to $Z_{11}$ are as defined in 8), can be obtained from the polyanion according to the invention by analogy with the methods disclosed in Patent Application EP 194,972.

It is understood that the cyclosporin derivatives obtained can optionally be converted to salts, when they exist.

The cyclosporin derivatives as defined in 1), 2), 3), 4), and 7) are of use in the treatment and/or the prophylaxis of retrovirus infections and more typically of AIDS (acquired immunodeficiency syndrome) and of associated syndromes [ARC (AIDS related complex)]. They exhibit the advantage of being slightly immunosuppressing.

The cyclosporin derivatives as defined in 5) exhibit an immunosuppressant activity and are thus of use in the treatment of various chronic inflammatory diseases and autoimmune diseases.

The cyclosporin derivatives as defined in 6) and in 8) have:

either an immunosuppressant activity, and they are thus of use in the treatment and/or the prophylaxis of autoimmune diseases or in preventing rejection of transplanted organs; or an antiinflammatory activity, and they are thus of use in the treatment of inflammations, such as, for example, arthritis and rheumatic diseases; or an antiparasitic activity, and they are, for example, of use in the treatment of schistosomiasis, filariasis, leishmaniasis, coccidioidomycosis, or malaria.

The following examples, given without implied limitation, illustrate the present invention.

EXAMPLE 1

Preparation of [(R)-2-(N,N-dimethylamino)ethylthio-Sar]$^3$-[4'-hydroxy-MeLeu]$^4$-cyclosporin A 68 cm$^3$ of toluene and 40 cm$^3$ of TBME ether were introduced into a reactor, under a nitrogen atmosphere, maintained at −20° C., and comprising a solution of 36.8 g of hexamethyldisilazane lithium salt in 104 cm$^3$ of TBME. A portion of 9.6 g of [4'-hydroxy-MeLeu]$^4$-cyclosporin A was added with stirring. The mixture was stirred for 15 minutes at a temperature in the region of −20° C. and then 8.3 g of caesium chloride were added in one portion. The reaction mixture was stirred for 30 minutes and then 25.5 g of di[2-(N,N-dimethylamino)ethyl] disulphide were added over 30 minutes. The reaction mixture was then brought to a temperature in the region of 25° C. over approximately 1 hour and 30 minutes. After stirring for 2 hours, the reaction mixture was cooled to a temperature in the region of −10° C. and 14.4 cm$^3$ of acetic acid were run in. Finally, 200 ml of water were added without maintaining the temperature and then the organic phase was separated off after separating by settling.

HPLC (High Performance Liquid Chromatography) analysis with external standardization of the organic phase showed that the reaction mixture comprised 3.95 g of

[(R)-2-(N,N-dimethylamino)ethylthio-Sar]³-[4'-hydroxy-MeLeu]⁴-cyclosporin A, which corresponds to a molar yield of 38%.

[(R)-2-(N,N-Dimethylamino)ethylthio-Sar]³-[4'-hydroxy-MeLeu]⁴-cyclosporin A was isolated in the following way:

After addition of 100 cm³ of distilled water to the organic phase, the mixture was cooled to 5° C. The pH of the aqueous phase was brought to 6.5 over approximately 30 minutes with stirring by dropwise addition of methanesulphonic acid (approximately 21 cm³). 20 g of alumina were subsequently added to the organic phase, separated by settling, and the mixture was stirred for 10 minutes. The mixture was filtered and the solid recovered was rinsed with TBME. The organic phases were subsequently combined and 200 ml of distilled water were added. The pH was then adjusted to 2 by addition of methanesulphonic acid with stirring. The mixture was stirred for 1 hour and 50 cm³ of acetonitrile were added. Finally, the organic phase was separated by settling and then discarded. The aqueous phase was concentrated under reduced pressure (2.7 kPa) at a temperature in the region of 30° C. until the organic solvents were completely removed. The pH of the aqueous phase was then brought to 9 by addition of 20% aqueous ammonia solution with stirring. Crude [(R)-2-(N,N-dimethylamino)ethylthio-Sar]³-[4'-hydroxy-MeLeu]⁴-cyclosporin A then precipitated from the aqueous phase. After isolating by filtering the precipitate and then drying at 40° C. for approximately 12 hours under reduced pressure (2.7 kPa), 6 g of crude [(R)-2-(N,N-dimethylamino)ethylthio-Sar]³-[4'-hydroxy-MeLeu]⁴-cyclosporin A were obtained.

A portion of 1 g of crude [(R)-2-(N,N-dimethylamino)ethylthio-Sar]³-[4'-hydroxy-MeLeu]⁴-cyclosporin A was purified by chromatography on a silica column (0.63–0.20 mm; eluent: 85/15/1 acetonitrile/methanol/ammonia (20% aq.) by volume). The fractions comprising the expected product were concentrated to dryness under reduced pressure (2.7 kPa) and gave 0.4 g of [(R)-2-(N,N-dimethylamino)ethylthio-Sar]³-[4'-hydroxy-MeLeu]⁴-cyclosporin A in the form of a white solid.

$^1$H NMR spectrum (400 MHz, CDCl$_3$, δ in ppm): 1.23 (d, J=7 Hz, 3H, 8β CH$_3$), 1.33 (d, J=7.5 Hz, 3H, 7β CH$_3$), 1.60 (d, J=5 Hz, 3H, 1η CH$_3$), 1.68 and 2.36 (2 dd, J=15 and 6.5 Hz, each 1H, 4β CH$_2$), 2.23 (broad s, 6H, N(CH$_3$)$_2$ of the 2-dimethylaminoethylthio at 3α), 2.40 (mt, 1H, 5β CH), from 2.50 to 2.85 (mt, 4H, SCH$_2$CH$_2$N of the 2-dimethylaminoethylthio at 3α), 2.68, 3.09, 3.16, 3.22, 3.42, and 3.47 (6s, respectively 6H, 3H, 3H, 3H, 3H and 3H, 7 NCH$_3$), 3.63 (d, J=6 Hz, 1H, OH at 1β), 3.72 (mt, 1H, 1β CH), 4.52 (mt,1H, 7α CH), 4.61 (t, J=9 Hz, 1H, 5α CH), 4.81 (mt, 1H, 8α CH), 4.95 (dd, J=9 and 6 Hz, 1H, α CH of a leucine), from 5.00 to 5.10 (mt, 2H, 2α CH and α CH of a leucine), 5.10 (d, J=11 Hz, 1H, 11α CH), from 5.20 to 5.35 (mt, 2H, CH=CH), 5.40 (t, J=6.5 Hz, 1H, 4α CH), 5.47 (d, J=6Hz, 1H, 1α CH), 5.68 (dd, J=10.5 and 4Hz, 1H, α CH of a leucine), 5.96 (s, 1H, 3α CH), 7.12 (d, J=8 Hz, 1H, CONH at 8), 7.46 (d, J=9 Hz, 1H, CONH at 5), 7.60 (d, J=7.5 Hz, 1H, CONH at 7), 7.92 (d, J=9.5 Hz, 1H, CONH at 2).

EXAMPLE 2

Preparation of the methanesulphonate salt of [(R)-2-(N,N-dimethylamino)ethylthio-Sar]³-cyclosporin A 38 cm³ of toluene and 25 cm³ of TBME were introduced into a reactor, under a nitrogen atmosphere, maintained at −20° C. comprising a solution of 20.8 g of hexamethyldisilazane lithium salt in 58 cm³ of TBME. 5.1 g of cyclosporin A were added in one portion with stirring, followed by 15 cm³ of TBME. The mixture was stirred for 15 minutes at a temperature in the region of −20° C. and then 4.4 g of caesium chloride were added in one portion. The reaction mixture was stirred for 30 minutes and then 13.9 g of di[2-(N,N-dimethylamino)ethyl] disulphide were added over 10 minutes. The reaction mixture was brought to a temperature in the region of 25° C. over approximately 1 hour and 30 minutes. After stirring for 1 hour, the reaction mixture was cooled to a temperature of approximately −10° C. and 10 cm³ of acetic acid were run in. Finally, 75 cm³ of water were added without maintaining the temperature and then the organic phase was separated by settling.

HPLC analysis with external standardization of the organic phase showed that the reaction mixture comprised 2.9 g of [(R)-2-(N,N-dimethylamino)ethylthio-Sar]³-cyclosporin A, which corresponds to a molar yield of 53%.

The methanesulphonate salt of [(R)-2-(N,N-dimethylamino)ethylthio-Sar]³-cyclosporin A was isolated in the following way:

The organic phase obtained above was concentrated to dryness under reduced pressure (2.7 kPa) at a temperature in the region of 35° C. The orange oily residue obtained (16.13 g) was treated with 240 cm³ of diethyl ether, 1.3 liters of distilled water, and 40 cm³ of 5N hydrochloric acid. The organic phase was separated by settling and discarded.

The aqueous phase was extracted with 250 cm³ of diethyl ether and it was then neutralized by addition of solid sodium bicarbonate until saturated. The said neutralized aqueous phase was then extracted with 250 cm³ of diethyl ether. The organic phase was separated by settling and separated off, and the aqueous phase was again extracted with 250 cm³ of diethyl ether.

The combined organic phases were washed with a total of 180 cm³ of a saturated sodium chloride solution, dried over sodium sulphate, and then filtered. The filtrate was concentrated to dryness under reduced pressure (2.7 kPa) at a temperature in the region of 30° C. and yielded 4.5 g of crude [(R)-2-(N,N-dimethylamino)ethylthio-Sar]³-cyclosporin A in the form of a cream foam. A portion of 1 g of the crude [(R)-2-(N,N-dimethylamino)ethylthio-Sar]³-cyclosporin A was purified by chromatography on a column of neutral alumina (eluent: ¼ cyclohexane/ethyl acetate by volume). The fractions comprising the expected product were combined and concentrated to dryness under reduced pressure (2.7 kPa) at a temperature in the region of 35° C. and gave 0.4 g of a white foam. The [(R)-2-(N,N-dimethylamino)ethylthio-Sar]³-cyclosporin A obtained was rechromatographed on a column of neutral alumina (eluent: ¼ cyclohexane/ethyl acetate by volume). The fractions comprising the expected product were combined and concentrated to dryness under reduced pressure (2.7 kPa) at a temperature in the region of 35° C. and gave 0.1 g of a white foam.

The said white foam was dissolved in 0.5 cm³ of diethyl ether. 0.4 cm³ of a 0.2N solution of methanesulphonic acid in diethyl ether was added to this solution. After stirring for 1 hour at a temperature in the region of 20° C., the mixture was filtered. The solid was rinsed with 2 times 0.1 cm³ of diethyl ether. After drying the solid to constant weight under reduced pressure (2.7 kPa) at a temperature in the region of 30° C. for 24 hours, 0.06 g of methanesulphonate salt of [(R)-2-(N,N-dimethylamino)ethylthio-Sar]³-cyclosporin A was obtained in the form of a white solid.

¹H NMR spectrum (400 MHz, (CD₃)₂SO, δ in ppm): 1.21 (d, J=7.5 Hz, 3H, 8β CH₃), 1.29 (d, J=7.5 Hz, 3H, 7β CH₃), 1.69 (d, J=6.5 Hz, 3H, 1η CH₃), 1.99 (mt,1H, 5β CH), 2.35 (s, 3H, CH₃ of the methanesulphonate), from 2.45 to 2.70 (mt, 2H, SCH₂ of the 2-dimethylaminoethylthio at 3α), 2.64, 2.80, 2.86, 2.93, 2.99, and 3.17 (6s, respectively 3H, 6H, 9H, 3H, 3H and 3H, 7 NCH₃ and NCH₃ of the 2-dimethylaminoethylthio at 3α), from 3.25 to 3.40 (mt, 2H, CH₂N of the 2-dimethylaminoethylthio at 3α), 3.99 (mt, 1H, 1β CH), 4.15 (mt, 1H, 7α CH), 4.26 (t, J=9 Hz, 1H, 5α CH), 4.42 (broad s, 1H, 1β at OH), 4.79 (mt, 1H, 8α CH), 4.89 (mt, 1H, 2α CH), from 5.00 to 5.15 (mt, 1H, α CH of a leucine), 5.11 (d, J=11 Hz, 1H, 11α CH), 5.23 (mt, 2H, 1α CH and α CH of a leucine), 5.33 (dd, J=10 and 5 Hz, 1H, α CH of a leucine), from 5.30 to 5.50 and 5.62 (2 mts, each 1H, CH═CH), 5.48 (dd, J=11 and 5 Hz,1H, α CH of a leucine), 6.87 (s, 1H, 3α CH), 7.64 (d, J=7.5 Hz, 1H, CONH at 7), 8.24 (d, J=9.5 Hz, 1H, CONH at 2), 8.28 (d, J=8 Hz, 1H, CONH at 8), 8.68 (d, J=9 Hz, 1H, CONH at 5), 9.28 (unresolved peak, 1H, SO₃H of the methanesulphonate).

EXAMPLE 3

Preparation of [(R)-methylthio-Sar]³-[4'-hydroxy-MeLeu]⁴-cyclosporin A 85 cm³ of tetrahydrofuran and 22.5 cm³ of toluene were introduced into a reactor, under a nitrogen atmosphere, maintained at −20° C., and comprising 19 g of hexamethyldisilazane lithium salt. 4.8 g of cyclosporin A were added in one portion with stirring, followed by 10 cm³ of tetrahydrofuran. The mixture was stirred for 15 minutes at a temperature in the region of −20° C. and then 4.46 g of caesium chloride were added in one portion. The reaction mixture was stirred for 15 minutes and then 5.8 g of dimethyl disulphide were added over approximately 15 minutes. The reaction mixture was brought to a temperature in the region of 25° C. over approximately 2 hours 30 minutes. After stirring for 4 hours, the reaction mixture was cooled to a temperature in the region of −10° C. and 10 cm³ of acetic acid were run in. 75 cm³ of water were added without maintaining the temperature and then the organic phase was separated by settling. HPLC analysis with external standardization of the organic phase showed that the reaction mixture comprised 2.3 g of [(R)-methylthio-Sar]³-[4'-hydroxy-MeLeu]⁴-cyclosporin A, which corresponds to a molar yield of 46%.

[(R)-Methylthio-Sar]³-[4'-hydroxy-MeLeu]⁴-cyclosporin A was isolated in the following way:

500 cm³ of water were added to the organic phase obtained above. 40 cm³ of 5N hydrochloric acid were run in with stirring over approximately 15 minutes. After stirring for 15 minutes, the organic phase was separated by settling and then concentrated to dryness under reduced pressure (2.7 kPa) at a temperature in the region of 35° C. 6.3 g of crude [(R)-methylthio-Sar]³-[4'-hydroxy-MeLeu]⁴-cyclosporin A were then obtained in the form of a yellowish foam.

A portion of 0.1 g of crude [(R)-methylthio-Sar]³-[4'-hydroxy-MeLeu]⁴-cyclosporin A was purified by preparative silica thin layer chromatography (eluent: 65/25/10 dichloromethane/acetonitrile/2-propanol by volume). The silica comprising the expected product was removed and stirred with 5 cm³ of dichloromethane. After filtering and evaporating under reduced pressure (2.7 kPa) at a temperature in the region of 30° C., 0.035 g of [(R)-methylthio-Sar]³-[4'-hydroxy-MeLeu]⁴-cyclosporin A was obtained in the form of a colourless film.

¹H NMR spectrum (400 MHz, CDCl₃, δ in ppm): 1.27 (d, J=7 Hz, 3H, 8β CH₃), 1.37 (d, J=7.5 Hz, 3H, 7β CH₃),1.64 (d, J=5 Hz, 3H, 1η CH₃), from 1.65 to 1.80 and 2.41 (respectively mt and dd, J=15 and 6.5 Hz, each 1H, 4β CH₂), 2.17 (s, 3H, SCH₃), 2.47 (mt, 1H, 5β CH), 2.71, 3.13, 3.18, 3.27, 3.46, and 3.52 (6s, respectively 6H, 3H, 3H, 3H and 3H, 7 NCH₃), 3.70 (d, J=6.5 Hz,1H, OH at 1β), 3.78 (mt, 1H, 1β CH), 4.56 (mt, 1H, 7α CH), 4.67 (t, J=9 Hz, 1H, 5α CH), 4.86 (mt, 1H, 8α CH), 5.00 (dd, J=9 and 6 Hz, 1H, α CH of a leucine), from 5.05 to 5.15 (mt, 2H, 2α CH and α CH of a leucine), 5.15 (d, J=11 Hz, 1H, 11α CH), from 5.25 to 5.40 (mt, 2H, CH═CH), 5.45 (t, J=6.5 Hz, 1H, 4α CH), 5.52 (d, J=6 Hz, 1H, 1α CH), 5.72 (dd, J=10.5 and 4 Hz, 1H, α CH of a leucine), 5.75 (s, 1H, 3α CH), 7.16 (d, J=8 Hz, 1H, CONH at 8), 7.52 (d, J=9 Hz, 1H, CONH at 5), 7.65 (d, J=7.5 Hz, 1H, CONH at 7), 7.94 (d, J=9.5 Hz, 1H, CONH at 2).

EXAMPLE 4

By carrying out the preparation in a way analogous to the method described in the preceding examples, the following products were prepared:

[(R)-2-aminoethylthio-Sar]³-cyclosporin A;
[(R)-2-(N-methylamino)ethylthio-Sar]³-cyclosporin A;
[(R)-2-(N-ethylamino)ethylthio-Sar]³-cyclosporin A;
[(R)-2-(N-isopropylamino)ethylthio-Sar]³-cyclosporin A;
[(R)-2-(N-isobutylamino)ethylthio-Sar]³-cyclosporin A;
[(R)-2-(N-t-butylamino)ethylthio-Sar]³-cyclosporin A;
[(R)-2-(N-phenylamino)ethylthio-Sar]³-cyclosporin A;
[(R)-2-(N-benzylamino)ethylthio-Sar]³-cyclosporin A;
[(R)-2-(N-methyl-N-ethylamino)ethylthio-Sar]³-cyclosporin A;
[(R)-2-(N-methyl-N-allylamino)ethylthio-Sar]³-cyclosporin A;
[(R)-2-(N-methyl-N-phenylamino)ethylthio-Sar]³-cyclosporin A;
[(R)-2-(N,N-diisopropylamino)ethylthio-Sar]³-cyclosporin A;
[(R)-2-(N,N-diallylamino)ethylthio-Sar]³-cyclosporin A;
[(R)-3-aminopropylthio-Sar]³-cyclosporin A;
[(R)-3-(N-methylamino)propylthio-Sar]³-cyclosporin A;
[(R)-3-(N-ethylamino)propylthio-Sar]³-cyclosporin A;
[(R)-3-(N-isopropylamino)propylthio-Sar]³-cyclosporin A;
[(R)-3-(N-t-butylamino)propylthio-Sar]³-cyclosporin A;
[(R)-3-(N-phenylamino)propylthio-Sar]³-cyclosporin A;
[(R)-3-(N-benzylamino)propylthio-Sar]³-cyclosporin A;
[(R)-3-(N-methyl-N-ethylamino)propylthio-Sar]³-cyclosporin A;
[(R)-3-(N-methyl-N-isopropylamino)propylthio-Sar]³-cyclosporin A;
[(R)-3-(N-methyl-N-t-butylamino)propylthio-Sar]³-cyclosporin A;
[(R)-3-(N-methyl-N-allylamino)propylthio-Sar]³-cyclosporin A;
[(R)-3-(N-methyl-N-phenylamino)propylthio-Sar]³-cyclosporin A;
[(R)-3-(N-methyl-N-benzylamino)propylthio-Sar]³-cyclosporin A;
[(R)-3-(N,N-diethylamino)propylthio-Sar]³-cyclosporin A;
[(R)-3-(N,N-diisopropylamino)propylthio-Sar]³-cyclosporin A;
[(R)-3-(N,N-diallylamino)propylthio-Sar]³-cyclosporin A;
[(R)-3-(1-piperidyl)propylthio-Sar]³-cyclosporin A;

[(R)-4-aminobutylthio-Sar]$^3$-cyclosporin A;
[(R)-4-(N-methylamino)butylthio-Sar]$^3$-cyclosporin A;
[(R)-4-(N-ethylamino)butylthio-Sar]$^3$-cyclosporin A;
[(R)-4-(N-isopropylamino)butylthio-Sar]$^3$-cyclosporin A;
[(R)-4-(N-t-butylamino)butylthio-Sar]$^3$-cyclosporin A;
[(R)-4-(N-phenylamino)butylthio-Sar]$^3$-cyclosporin A;
[(R)-4-(N-benzylamino)butylthio-Sar]$^3$-cyclosporin A;
[(R)-4-(N-methyl-N-ethylamino)butylthio-Sar]$^3$-cyclosporin A;
[(R)-4-(N-methyl-N-isopropylamino)butylthio-Sar]$^3$-cyclosporin A;
[(R)-4-(N-methyl-N-t-butylamino)butylthio-Sar]$^3$-cyclosporin A;
[(R)-4-(N-methyl-N-allylamino)butylthio-Sar]$^3$-cyclosporin A;
[(R)-4-(N-methyl-N-phenylamino)butylthio-Sar]$^3$-cyclosporin A;
[(R)-4-(N-methyl-N-benzylamino)butylthio-Sar]$^3$-cyclosporin A;
[(R)-4-(N,N-dimethylamino)butylthio-Sar]$^3$-cyclosporin A;
[(R)-4-(N,N-diethylamino)butylthio-Sar]$^3$-cyclosporin A;
[(R)-4-(N,N-diisopropylamino)butylthio-Sar]$^3$-cyclosporin A;
[(R)-4-(N,N-diallylamino)butylthio-Sar]$^3$-cyclosporin A;
[(R)-4-(1-piperidyl)butylthio-Sar]$^3$-cyclosporin A;
[(R)-2-amino-2-methylpropylthio-Sar]$^3$-cyclosporin A;
[(R)-2-(N,N-dimethylamino)-2-methylpropylthio-Sar]$^3$-cyclosporin A;
[(R)-2-(N,N-diethylamino)-2-methylpropylthio-Sar]$^3$-cyclosporin A;
[(R)-2-(1-piperidyl-2-methylpropylthio-Sar]$^3$-cyclosporin A;
[(R)-3-amino-3-methylbutylthio-Sar]$^3$-cyclosporin A;
[(R)-3-(N,N-dimethylamino)-3-methylbutylthio-Sar]$^3$-cyclosporin A;
[(R)-3-(N,N-diethylamino)-3-methylbutylthio-Sar]$^3$-cyclosporin A;
[(R)-3-(1-piperidyl)-3-methylbutylthio-Sar]$^3$-cyclosporin A;
[(R)-2-(1-morpholino)ethylthio-Sar]$^3$-cyclosporin A;
[(R)-2-(1-azetidino)ethylthio-Sar]$^3$-cyclosporin A;
{(R)-2-[1-(4-methylpiperazino)]ethylthio-Sar}$^3$-cyclosporin A;
{(R)-2-[l-(4-phenylpiperazino)]ethylthio-Sar}$^3$-cyclosporin A;
{(R)-2-[l-(4-benzylpiperazino)]ethylthio-Sar}$^3$-cyclosporin A;
{(R)-2-[1 -(4-methyl-1,2,3,6-tetrahydropyridyl)]ethylthio-Sar}$^3$-cyclosporin A;
{(R)-2-[1-(4-phenyl-1,2,3,6-tetrahydropyridyl)]ethylthio-Sar}3-cyclosporin A;
[(R)-3-(1-morpholino)propylthio-Sar]$^3$-cyclosporin A;
[(R)-3-(1-azetidino) propylthio-Sar]$^3$-cyclosporin A;
{(R)-3-[1-(4-methylpiperazino)]propylthio-Sar}$^3$-cyclosporin A;
{(R)-3-[1-(4-phenylpiperazino)]propylthio-Sar}$^3$-cyclosporin A;
{(R)-3-[1-(4-benzylpiperazino)]propylthio-Sar}$^3$-cyclosporin A;
{(R)-3-[1-(4-methyl-1,2,3,6-tetrahydropyridyl)]propylthio-Sar}$^3$-cyclosporin A;
{(R)-3-[1-(4-phenyl-1,2,3,6-tetrahydropyridyl)]propylthio-Sar}$^3$-cyclosporin A;
[(R)-2-aminoethylthio-Sar]$^3$-[4'-hydroxy-MeLeu]$^4$-cyclosporin A;
[(R)2-(N-methylamino)ethylthio-Sar]$^3$-[4'-hydroxy-MeLeu]$^4$-cyclosporin A;
[(R)-2-(N-ethylamino)ethylthio-Sar]$^3$-[4'-hydroxy-MeLeu]$^4$-cyclosporin A;
[(R)-2-(N-isopropylamino)ethylthio-Sar]$^3$-[4'-hydroxy-MeLeu]$^4$-cyclosporin A;
[(R)-2-(N-t-butylamino)ethylthio-Sar]$^3$-[4'-hydroxy-MeLeu]$^4$-cyclosporin A;
[(R)-2-(N-phenylamino)ethylthio-Sar]$^3$-[4'-hydroxy-MeLeu]$^4$-cyclosporin A;
[(R)-2-(N-benzylamino)ethylthio-Sar]$^3$-[4'-hydroxy-MeLeu]$^4$-cyclosporin A;
[(R)-2-(N-methyl-N-ethylamino)ethylthio-Sar]$^3$-[4'-hydroxy-MeLeu]$^4$-cyclosporin A;
[(R)-2-(N-methyl-N-isopropylamino)ethylthio-Sar]$^3$-[4'-hydroxy-MeLeu]$^4$-cyclosporin A;
[(R)-2-(N-methyl-N-tert-butylamino)ethylthio-Sar]$^3$-[4'-hydroxy-MeLeu]$^4$-cyclosporin A;
[(R)-2-(N-methyl-N-allylamino)ethylthio-Sar]$^3$-[4'-hydroxy-MeLeu]$^4$-cyclosporin A;
[(R)-2-(N-methyl-N-phenylamino)ethylthio-Sar]$^3$-[4'-hydroxy-MeLeu]$^4$-cyclosporin A;
[(R)-2-(N-methyl-N-benzylamino)ethylthio-Sar]$^3$-[4'-hydroxy-MeLeu]$^4$-cyclosporin A;
[(R)-2-(N,N-diethylamino)ethylthio-Sar]$^3$-[4'-hydroxy-MeLeu]$^4$-cyclosporin A;
[(R)-2-(N,N-diisopropylamino)ethylthio-Sar]$^3$-[4'-hydroxy-MeLeu]$^4$-cyclosporin A;
[(R)-2-(N,N-diallylthio-Sar]$^3$-[4'-hydroxy-MeLeu]$^4$-cyclosporin A;
[(R)-2-(1-piperidyl)ethylthio-Sar]$^3$-[4'-hydroxy-MeLeu]$^4$-cyclosporin A;
[(R)-3-aminopropylthio-Sar]$^3$-[4'-hydroxy-MeLeu]$^4$-cyclosporin A;
[(R)-3-(N-methylamino)propylthio-Sar]$^3$-[4'-hydroxy-MeLeu]$^4$-cyclosporin A;
[(R)-3-(N-ethylamino)propylthio-Sar]$^3$-[4'-hydroxy-MeLeu]$^4$-cyclosporin A;
[(R)-3-(N-isopropylamino)propylthio-Sar]$^3$-[4'-hydroxy-MeLeu]$^4$-cyclosporin A;
[(R)-3-(N-tert-butylamino)propylthio-Sar]$^3$-[4'-hydroxy-MeLeu]$^4$-cyclosporin A;
[(R)-3-( N-phenylamino)propylthio-Sar]$^3$-[4'- hydroxy-MeLeu]$^4$-cyclosporin A;
[(R)-3-(N-benzylamino)propylthio-Sar]$^3$-[4'-hydroxy-MeLeu]$^4$-cyclosporin A;
[(R)-3-(N-methyl-N-ethylamino)propylthio-Sar]$^3$-[4'-hydroxy-MeLeu]$^4$-cyclosporin A;
[(R)-3-(N-methyl-N-isopropylamino)propylthio-Sar]$^3$-[4'-hydroxy-MeLeu]$^4$-cyclosporin A;
[(R)-3-(N-methyl-N-allylamino)propylthio-Sar]$^3$-[4'-hydroxy-MeLeu]$^4$-cyclosporin A;
[(R)-3-(N-methyl-N-phenylamino)propylthio-Sar]$^3$-[4'-hydroxy-MeLeu]$^4$-cyclosporin A;
[(R)-3-(N-methyl-N-benzylamino)propylthio-Sar]$^3$-[4'-hydroxy-MeLeu]$^4$-cyclosporin A;
[(R)-2-(N,N-dimethylamino)ethylthio-Sar]$^3$-[4'-hydroxy-MeLeu]$^4$-cyclosporin A;
[(R)-3-(N,N-diethylamino)propylthio-Sar]$^3$-[4'-hydroxy-MeLeu]$^4$-cyclosporin A;
[(R)-3-(N,N-diisopropylamino)propylthio-Sar]$^3$-[4'-hydroxy-MeLeu]$^4$-cyclosporin A;
[(R)-3-(N,N-diallylamino)propylthio-Sar]$^3$-[4'-hydroxy-MeLeu]$^4$-cyclosporin A;
[(R)-3-(1-piperidyl)propylthio-Sar]$^3$-[4'-hydroxy- MeLeu]$^4$-cyclosporin A;
[(R)-4-aminobutylthio-Sar]$^3$-[4'-hydroxy-MeLeu]$^4$-cyclosporin A;

[(R)-4-(N-methylamino)butylthio-Sar]³-[4'-hydroxy-MeLeu]⁴-cyclosporin A;
[(R)-4-(N-ethylamino)butylthio-Sar]³-[4'-hydroxy-MeLeu]⁴-cyclosporin A;
[(R)-4-(N-isopropylamino)butylthio-Sar]³-[4'-hydroxy-MeLeu]⁴-cyclosporin A;
[(R)-4-(N-t-butylamino)butylthio-Sar]³-[4'-hydroxy-MeLeu]⁴-cyclosporin A;
[(R)-4-(N-phenylamino)butylthio-Sar]³ -[4'-hydroxy-MeLeu]⁴cyclosporin A;
[(R)-4-(N-benzylamino)butylthio-Sar]³-[4'-hydroxy-MeLeu]⁴-cyclosporin A;
[(R)-4-(N-methyl-N-ethylamino)butylthio-Sar]³-[4'-hydroxy-MeLeu]⁴-cyclosporin A;
[(R)-4-(N-methyl-N-isopropylamino)butylthio-Sar]³-[4'-hydroxy-MeLeu]⁴-cyclosporin A;
[(R)-4-(N-methyl-N-t-butylamino)butylthio-Sar]³-[4'-hydroxy- MeLeu]⁴-cyclosporin A;
[(R)-4-(N-methyl-N-allylamino)butylthio-Sar]³-[4'-hydroxy-MeLeu]⁴-cyclosporin A;
[(R)-4-(N-methyl-N-phenylamino)butylthio-Sar]³-[4'-hydroxy-MeLeu]⁴-cyclosporin A;
[(R)-4-(N-methyl-N-benzylamino)butylthio-Sar]³-[4'-hydroxy-MeLeu]⁴-cyclosporin A;
[(R)-4-(N,N-dimethylamino)butylthio-Sar]³-[4'-hydroxy-MeLeu]⁴- cyclosporin A;
[(R)-4-(N,N-diethylamino)butylthio-Sar]³-[4'-hydroxy-MeLeu]⁴-cyclosporin A;
[(R)-4-(N,N-diisopropylamino)butylthio-Sar]³-[4'-hydroxy-MeLeu]⁴-cyclosporin A;
[(R)-4-(N,N-diallylamino)butylthio-Sar]³-[4'-hydroxy-MeLeu]⁴-cyclosporin A;
[(R)-4-(1-piperidyl)butylthio-Sar]³-[4'-hydroxy-MeLeu]⁴-cyclosporin A;
[(R)-2-amino-2-methylpropylthio-Sar]³-[4'-hydroxy-MeLeu]⁴-cyclosporin A;
[(R)-2-(N,N-dimethylamino)-2-methylpropylthio-Sar]³-[4'-hydroxy-MeLeu]⁴-cyclosporin A;
[(R)-2-(N,N-diethylamino)-2-methylpropylthio-Sar]³-[4'-hydroxy-MeLeu]⁴-cyclosporin A;
[(R)-2-(1-piperidyl)-2-methylpropylthio-Sar]³-[4'-hydroxy-MeLeu]⁴-cyclosporin A;
[(R)-3-amino-3-methylbutylthio-Sar]³ -[4'-hydroxy-MeLeu]⁴-cyclosporin A;
[(R)-3-(N,N-dimethylamino)-3-methylbutylthio-Sar]³-[4'-hydroxy-MeLeu]⁴-cyclosporin A;
[(R)-3-(N,N-diethylamino)-3-methylbutylthio-Sar]³-[4 '-hydroxy-MeLeu]⁴-cyclosporin A;
[(R)-3-(1-piperidyl)-3-methylbutylthio-Sar]³-[4'-hydroxy-MeLeu]⁴-cyclosporin A;
[(R)-2-(1-morpholino)ethylthio-Sar]³-[4'-hydroxy-MeLeu]⁴-cyclosporin A;
[(R)-2-(1-azetidino)ethylthio-Sar]³-[4'- hydroxy-MeLeu]⁴-cyclosporin A;
{(R)-2-[1-(4-methylpiperazino)]ethylthio-Sar}³-[4'-hydroxy-MeLeu]⁴-cyclosporin A;
{(R)-2-[1-(4-phenylpiperazino)]ethylthio-Sar}³-[4'-hydroxy-MeLeu]⁴-cyclosporin A;
{(R)-2-[1-(4-benzylpiperazino)]ethylthio-Sar}³-[4'-hydroxy-MeLeu]⁴-cyclosporin A;
{(R)-2-[1-(4-methyl-1,2,3,6-tetrahydropyridyl)]ethylthio-Sar}³-[4'-hydroxy-MeLeu]⁴-cyclosporin A;
{(R)-2-[1-(4-phenyl-1,2,3,6-tetrahydropyridyl)]ethylthio-Sar}³-[4'-hydroxy -MeLeu]⁴-cyclosporin A;
[(R)-3-(1-morpholino)propylthio-Sar]³-[4'-hydroxy-MeLeu]⁴-cyclosporin A;
[(R)-3-(1-azetidino)propylthio-Sar]³-[4'-hydroxy-MeLeu]⁴-cyclosporin A;
{(R)-3-[1-(4-methylpiperazino)]propylthio-Sar}³-[4'-hydroxy-MeLeu]⁴-cyclosporin A;
{(R)-3-[1-(4-phenylpiperazino)]propylthio-Sar}³-[4'-hydroxy-MeLeu]⁴-cyclosporin A;
{(R)-3-[1-(4-benzylpiperazino)]propylthio-Sar}³-[4'-hydroxy-MeLeu]⁴-cyclosporin A;
{(R)-3-[1-(4-methyl-1,2,3,6-tetrahydropyridyl)]propylthio-Sar}3-[4'-hydroxy-MeLeu]⁴-cyclosporin A; and
{(R)-3-[1-(4-phenyl-1,2,3,6-tetrahydropyridyl)]propylthio-Sar}3-[4'-hydroxy-MeLeu]⁴-cyclosporin A.

The invention claimed is:

1. A process for preparing a polyanion for use as an intermediate in the preparation of a cyclosporin derivative, said process comprising treating a cyclosporin with a hexamethyldisilazane metal salt and a metal halide to form said polyanion, wherein said polyanion has the formula:

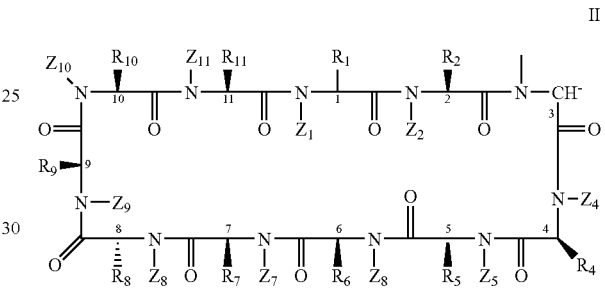

in which
the radicals $R_1$, $R_2$, and $R_4$ to $R_{11}$, and $Z_1$, $Z_2$, and $Z_4$ to $Z_{11}$, are defined as for cyclosporin A, with the exception of $R_4$ and $Z_4$, which are defined so as to have, at the 4-position, the amino acid 4'-hydroxy-methylleucine.

2. The process according to claim 1, in which said hexamethyldisilazane metal salt is a hexamethyldisilazane alkali metal salt.

3. A process according to claim 2, in which said hexamethyldisilazane metal salt is chosen from the hexamethyldisilazane lithium salt, the hexamethyldisilazane sodium salt, and the hexamethyldisilazane potassium salt.

4. The process according to claim 3, in which said hexamethyldisilazane metal salt is used in an amount ranging from 20 to 30 molar equivalents.

5. The process according to claim 1, in which, when the treatment of the cyclosporin is carried out in the presence of a metal halide, said metal halide is chosen from lithium chloride, caesium chloride, caesium fluoride, cuprous chloride, and mercuric chloride.

6. The process according to claim 5, in which, when said metal halide is caesium chloride or lithium chloride, it is used in an amount ranging from 2 to 8 molar equivalents.

7. The process according to claim 6, in which the treatment of the cyclosporin is carried out in an aliphatic or cyclic ether, an aromatic hydrocarbon, or a mixture of these solvents.

8. The process according to claim 7, in which the treatment of the cyclosporin is carried out at a temperature ranging from –40° C. to 0° C.

9. The process according to claim 8, in which the treatment of the cyclosporin is carried out with a ratio (weight/ weight) of cyclosporin involved with respect to the total weight of the solution which is less than or equal to 10%.

10. A process for preparing a cyclosporin derivative substituted at the 3-position, said process comprising preparing a polyanion by treating a cyclosporin with a hexamethyldisilazane metal salt, optionally in the presence of a metal halide, wherein the treatment of the cyclosporin is carried out at a temperature ranging from −40° C. to 0° C., adding an electrophilic agent to said treated cyclosporin, and, optionally converting the product of said addition to a salt, in which at least one obtained cyclosporin derivative substituted at the 3-position has the formula:

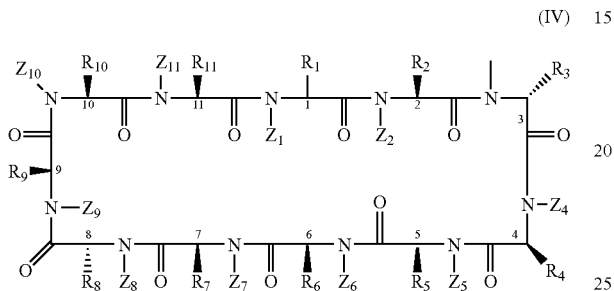

(IV)

in which the radicals $R_1$, $R_2$, and $R_4$ to $R_{11}$, and $Z_1$, $Z_2$, and $Z_4$ to $Z_{11}$ are defined as for cyclosporin A, with the exception of $R_4$ and $Z_4$, which are defined so as to have, at the 4-position, the amino acid 4'-hydroxy-methylleucine, and of $R_3$, which is —S—OH$_3$ or a radical —S-Alk-R° in which:

- Alk is an alkylene radical comprising from 2 to 6 straight- or branched-chain carbon atoms or a cycloalkylene radical comprising from 3 to 6 carbon atoms; and
- R° is
  - a hydroxyl, carboxyl, or alkyloxycarbonyl radical; or
  - an —NG$_1$G$_2$ radical or a radical of formula:

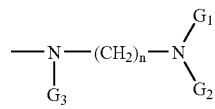

(V)

in which $G_1$ and $G_2$, which are identical or different, are
- each a hydrogen atom; or
- a phenyl, cycloalkyl ($C_{3-6}$), alkenyl ($C_{2-4}$), or alkyl radical, each of which is optionally substituted by a halogen atom, an alkyloxy, alkyloxycarbonyl, amino, alkylamino, or dialkylamino radical; or
- a benzyl radical or a saturated or unsaturated heterocyclyl radical comprising 5 or 6 ring members and from 1 to 3 heteroatoms; or
- $G_1$ and $G_2$ form, with the nitrogen atom to which they are attached, a saturated or unsaturated heterocycle comprising from 4 to 6 ring members which can comprise another heteroatom chosen from nitrogen, oxygen, and sulphur and which is optionally substituted by alkyl, phenyl, or benzyl; and
- $G_3$ is a hydrogen atom or an alkyl radical, and n is an integer from 2 to 4, the alkyl portions or radicals defined above are straight or branched and comprise from 1 to 4 carbon atoms.

11. The process according to claim 10, wherein said cyclosporin derivative substituted at the 3-position is [(R)-2-(N,N-dimethylamino)ethylthio-Sar]$^3$-[4'-hydroxy-Me-Leu]$^4$-cyclosporin A.

12. The process of claim 10, in which at least one hydroxyl radical present on said cyclosporin that interferes with the treating reaction is protected before said treatment with a protective radical and then the protective radicals are removed after said treatment.

* * * * *

UNITED STATES PATENT AND TRADEMARK OFFICE
CERTIFICATE OF CORRECTION

PATENT NO. : 7,226,905 B2  Page 1 of 1
APPLICATION NO. : 09/742008
DATED : June 5, 2007
INVENTOR(S) : Christian Viskov It is certified that error appears in the above-identified patent and that said Letters Patent is hereby corrected as shown below:

In claim 1, column 18, line 36, "$Z_{11}$, are" should read --$Z_{11}$ are--.

In claim 10, column 19, line 31, "-S-OH$_3$" should read ---S-CH$_3$--.

Signed and Sealed this

Eighteenth Day of March, 2008

JON W. DUDAS
*Director of the United States Patent and Trademark Office*